United States Patent
Oh et al.

(10) Patent No.: US 8,867,822 B2
(45) Date of Patent: Oct. 21, 2014

(54) MODEL-BASED CORONARY ARTERY CALCIUM SCORING

(75) Inventors: Seungseok Oh, Los Angeles, CA (US); Daniel Russakoff, San Francisco, CA (US)

(73) Assignee: FUJIFILM Corporation, Tokyo (JP)

( * ) Notice: Subject to any disclaimer, the term of this patent is extended or adjusted under 35 U.S.C. 154(b) by 320 days.

(21) Appl. No.: 13/274,055

(22) Filed: Oct. 14, 2011

(65) Prior Publication Data

US 2013/0094749 A1   Apr. 18, 2013

(51) Int. Cl.
| | |
|---|---|
| *G06K 9/00* | (2006.01) |
| *A61B 6/00* | (2006.01) |
| *A61B 6/03* | (2006.01) |
| *G06T 7/00* | (2006.01) |

(52) U.S. Cl.
CPC ............... *A61B 6/03* (2013.01); *G06T 2200/04* (2013.01); *A61B 6/503* (2013.01); *A61B 6/504* (2013.01); *G06T 2207/20076* (2013.01); *G06T 2207/20084* (2013.01); *G06T 2207/30048* (2013.01); *G06T 2207/20101* (2013.01); *G06T 2207/10081* (2013.01); *G06T 2207/20081* (2013.01); *G06T 7/0012* (2013.01); *A61B 6/5217* (2013.01); *G06T 2207/30101* (2013.01)
USPC ........... 382/154; 382/100; 382/128; 382/130; 382/131; 382/224; 382/226; 382/309

(58) Field of Classification Search
CPC ... G06K 9/46; G06K 9/00208; G06K 9/4638; G06T 15/00; G06T 7/00; G06T 2207/10028; G06T 17/00; G06T 1/0007; G06T 2200/08; G06T 15/08; G06T 7/0012; G06T 7/602
USPC ......... 382/154, 100, 128, 130, 131, 224, 226, 382/309
See application file for complete search history.

(56) References Cited

U.S. PATENT DOCUMENTS

| | | |
|---|---|---|
| 6,233,304 B1 | 5/2001 | Hu et al. |
| 6,674,834 B1 | 1/2004 | Acharya et al. |
| 6,697,451 B2 | 2/2004 | Acharya et al. |
| 6,996,262 B2 | 2/2006 | Li |
| 7,127,096 B2 | 10/2006 | Kaufman et al. |
| 7,149,331 B1 | 12/2006 | Kaufman et al. |
| 7,330,576 B2 | 2/2008 | Raman et al. |

(Continued)

OTHER PUBLICATIONS

Agatston, Arthur S., et al., "Quantification of Coronary Artery Calcium Using Ultrafast Computed Tomography," JACC, Mar. 15, 1990, pp. 827-832, vol. 15, No. 4.

(Continued)

*Primary Examiner* — Mike Rahmjoo
(74) *Attorney, Agent, or Firm* — Sughrue Mion, PLLC

(57) ABSTRACT

A system and method are provided for model-based coronary artery calcium (CAC) scoring. A model image of a heart region is aligned with an image of a patient's heart region in order to more easily identify the coronary arteries and other relevant anatomical features in the image. Once the images are aligned, relevant calcium plaques are identified by their presence within a coronary artery, and the relevant plaques are then labeled by the specific coronary artery in which they are located. The coronary arteries with the labeled plaques are scored individually based on their size and X-ray attenuation, and an overall score based on all of the relevant plaques is then computed, which is related to the patient's risk for coronary artery disease.

16 Claims, 5 Drawing Sheets

(56) References Cited

U.S. PATENT DOCUMENTS

| | | |
|---|---|---|
| 7,340,083 B2 | 3/2008 | Yuan et al. |
| 7,409,079 B2 | 8/2008 | Saptharishi et al. |
| 7,558,611 B2 | 7/2009 | Arnold et al. |
| 7,957,574 B2 | 6/2011 | Sirohey et al. |
| 2004/0017936 A1 | 1/2004 | Gopinath et al. |
| 2004/0116796 A1 | 6/2004 | Li |
| 2006/0013640 A1 | 1/2006 | Skakoon et al. |
| 2008/0159610 A1 | 7/2008 | Haas et al. |
| 2009/0136107 A1 | 5/2009 | Arnold et al. |
| 2010/0049740 A1* | 2/2010 | Iwase et al. ............ 707/104.1 |
| 2011/0206247 A1* | 8/2011 | Dachille et al. ............ 382/128 |
| 2011/0249877 A1* | 10/2011 | Begelman et al. ............ 382/128 |

OTHER PUBLICATIONS

Rumberger, John A., et al., "A Rosetta Stone for Coronary Calcium Risk Stratification: Agatston, Volume, and Mass Scores in 11, 490 Individuals," AJR, Sep. 2003, pp. 743-748, vol. 181.

Isgum, I., et al., "A pattern recognition approach to automated coronary calcium scoring," Proceedings of the 17th International Conference on Pattern Recognition (ICPR), 2004, 4 pages.

* cited by examiner

RELATED ART

MODEL-BASED CORONARY ARTERY CALCIUM SCORING

BACKGROUND

1. Field

The systems and methods described below relate to the detection and scoring of calcium deposits in an artery, and more specifically to using an anatomical model image to improve detection, classification and scoring of coronary artery calcium.

2. Background

Medical imaging is the field of creating images of the human body for medical purposes, such as diagnosing or examining disease or other physiological anomalies. Numerous types of image modalities produce medical images, such as magnetic resonance imaging (MRI), radiography (x-rays), computed tomography (CT), ultrasound (US) and others. In medical imaging, an object of interest is usually selected pertaining to an area of the human body, such as the head, heart or chest.

FIGS. 1A and 1B illustrate a 3D CT image of a heart. In FIG. 1A, the image 402 illustrates the heart, while in FIG. 1B, the image 404 illustrates only the coronary arteries.

A common method for detecting coronary artery disease is to take a CT image of the chest region and quantify calcifications of the coronary artery and heart. The presence of calcifications, or calcium salts, in the vessel lining of the coronary arterial wall is a primary factor in detecting atherosclerosis, or the thickening of the artery wall, which leads to coronary artery disease. The number and amount of calcifications in particular is typically a sign of the amount of plaque, or debris, in the artery. Early detection of coronary artery disease through the use of the CT scan is a significant factor in reducing the high mortality rate of the disease.

In order to diagnose coronary artery disease using the CT scan, the number of calcifications must be identified and then "scored" in order to determine their significance. Coronary artery calcium (CAC) scoring is a time-consuming process, primarily because of the step of identifying whether each plaque is a relevant calcification and in which artery it is located. The identification step typically requires manual identification of each plaque by a cardiologist or highly-skilled technician.

A common scoring method to quantify calcifications is the Agatston Method, which provides a single score, the Agatston Score, which quantifies the total arterial calcium in the heart. Other scoring methods include volume scoring and mass scoring. In these methods and their variants, the process is essentially similar: 1) find plaques by thresholding, 2) identify whether each plaque is a relevant calcification inside a coronary artery (and if so, which artery), and 3) take a weighted sum.

Attempts to automate the calcium scoring process have been met with limited success. While some methods provide a single overall score, other methods attempt to provide individual scores for individual arteries. However, the methods for providing individual scores have trouble accurately identifying the correct artery and also detect false positives, which include irrelevant plaques (bony structures, noise, heart calcium outside vessels, etc.).

Thus, an accurate and robust method for coronary artery calcium scoring is needed.

SUMMARY

Various embodiments of the invention relate to systems and methods for model-based coronary artery calcium (CAC) scoring in a medical image, and more particularly to identifying the location of relevant calcium plaques inside particular coronary arteries by comparing an image of a patient's heart region with a model image of a heart region to aid in identifying the coronary arteries and other anatomical features on the image. Based on the comparison of the image with the model image, relevant calcium plaques can be identified and labeled based on their location within a particular coronary artery. A score is then computed for each relevant artery (e.g., coronary artery) in addition to an overall score for the entire heart region of the patient, thereby increasing the accuracy of an assessment of the patient's risk for coronary artery disease.

In one exemplary embodiment, a method for coronary artery calcium (CAC) scoring comprises a method for coronary artery calcium scoring, including, receiving an image of a heart which may include calcium plaque, and aligning anatomical features of the heart in the image with anatomical features of a model image to provide information on which area of the heart corresponds to realm of each of coronary arteries, which can be used later to provide the labeling step with information on which artery a plaque is most likely to be in and its likelihood. The method further includes, when plaques are present on the respective coronary arteries on the image of the heart, labeling plaques to the respective coronary arteries on the image of the heart, scoring determines individual scores of the respective coronary arteries and an overall score of the heart, and displaying the individual scores and the overall score.

According to another exemplary embodiment, a system for coronary artery calcium scoring includes an input unit which receives an image of a heart which may include calcium plaque, an alignment unit which aligns anatomical features of the heart in the image with anatomical features of a model image, and a labeling unit which labels, when plaques are present on the respective coronary arteries on the image of the heart, the plaques to the respective coronary arteries on the image of the heart. The system further includes a scoring unit which determines individual scores of the respective coronary arteries and an overall score of the heart, and a display unit which prepares a graphical user interface for displaying the individual scores and the overall score.

According to a further exemplary embodiment, a computer program product for coronary artery calcium scoring is provided. The computer program is product embodied on a computer readable medium and when executed by a computer, and performs a method that includes receiving an image of a heart which may include calcium plaque, aligning anatomical features of the heart in the image with anatomical features of a model image, and when plaques are present on the respective coronary arteries on the image of the heart, labeling plaques to respective coronary arteries on the image of the heart. The method further includes scoring individual scores of the respective coronary arteries and an overall score of the heart, and displaying at least one of the individual scores and the overall score.

In the foregoing exemplary embodiments, and as is well-known in the art, the heart may or may not contain plaque. Regardless of whether the heart contains plaque or not, the scoring is performed. If there is no CAC, then the score is zero. This can be the case for any of the individual arteries and/or the heart.

Additional embodiments related to the invention will be set forth in part in the description which follows, and in part will be apparent from the description, or may be learned by practice of the invention. Embodiments of the invention may be realized and attained by means of the elements and combinations of various elements and aspects particularly pointed out in the following detailed description and the appended claims.

It is to be understood that both the foregoing and the following descriptions are exemplary and explanatory only and are not intended to limit the claimed invention or application thereof in any manner whatsoever.

BRIEF DESCRIPTION OF THE DRAWINGS

The accompanying drawings, which are incorporated in and constitute a part of this specification exemplify various embodiments of the present invention and, together with the description, serve to explain and illustrate principles of the inventive technique. Specifically.

DETAILED DESCRIPTION

Figures 1A, 1B:
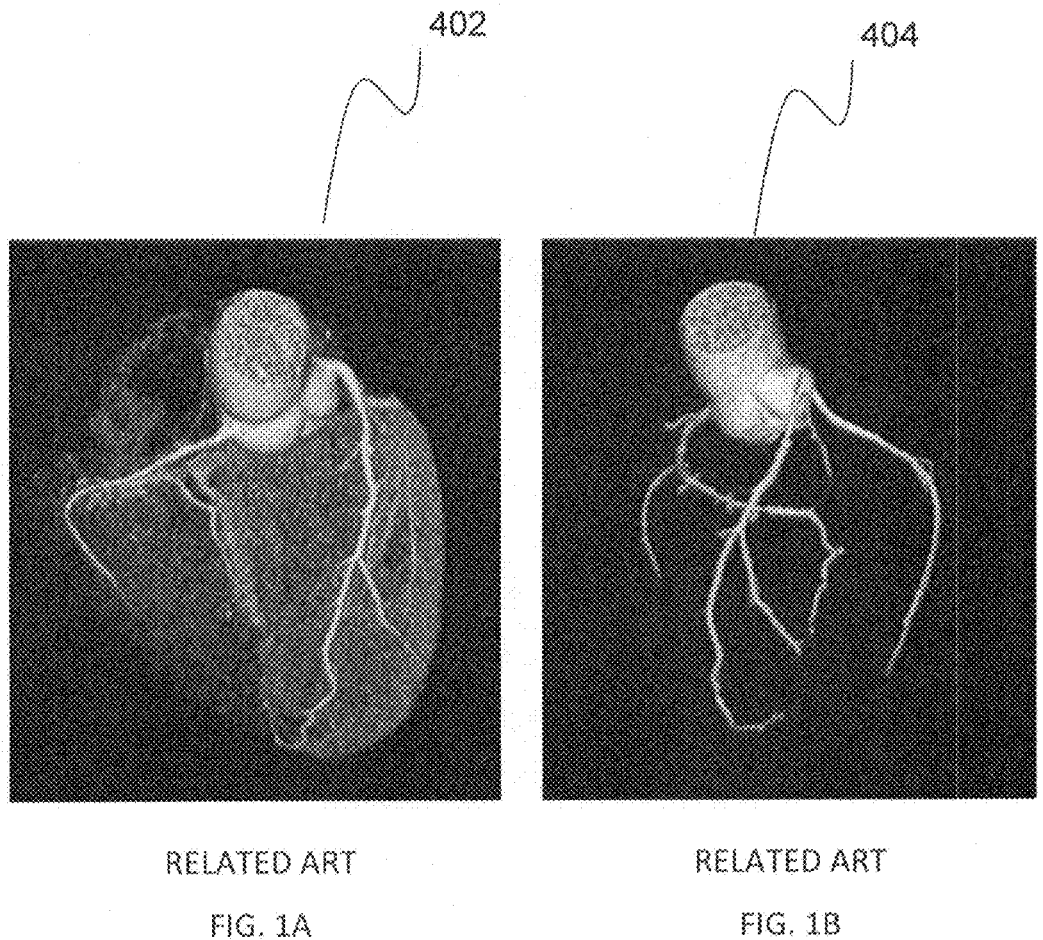
FIGS. 1A and 1B depict related art three-dimensional (3D) images of the heart illustrating the coronary arteries.

In the following detailed description, reference will be made to the accompanying drawing(s), in which identical functional elements are designated with like numerals. The aforementioned accompanying drawings show by way of illustration and not by way of limitation, specific embodiments and implementations consistent with principles of the present invention. These implementations are described in sufficient detail to enable those skilled in the art to practice the invention and it is to be understood that other implementations may be utilized and that structural changes and/or substitutions of various elements may be made without departing from the scope and spirit of present invention. The following detailed description is, therefore, not to be construed in a limited sense. Additionally, the various embodiments of the invention as described may be implemented in the form of software running on a general purpose computer, in the form of a specialized hardware, or combination of software and hardware. Expressions such as "at least one of," when preceding a list of elements, modifies the entire list of elements and does not modify each element of the list.

Embodiments of the invention automate calcium scoring for assessing coronary artery disease risk, and make the diagnosis and reporting of cardiac disease easier, more accurate and less time-consuming. A model-based approach is used to compare an image of a patient's heart region with a model image of the heart. The model image of the heart illustrates the coronary arteries and other anatomical features and/or provides each spatial area with the probability that a specific coronary artery is present in the area. This comparison aids in identifying whether calcium plaques are present within a coronary artery, and if so, in which one. Thus, irrelevant calcium plaques and other noise in the image can be ignored, and the relevant calcium plaques within the coronary arteries can be individually weighted to provide a more accurate and robust assessment of the patient's risk for coronary artery disease.

The model-based approach allows decisions to be made as to which of the four major coronary arteries a particular calcium plaque is located in. The four major coronary arteries are the left main (LM), left anterior descending (LAD), left circumflex (LCX) and right coronary artery (RCA). Calcium plaques that do not match with a coronary artery in the model can be ignored as irrelevant plaques and removed from consideration in subsequent scoring of the artery. A calcium score can then be calculated not only for the entire heart, but also for individual coronary arteries, as plaques can be labeled with arteries by comparison of the image with the model. If no plaque is found, the score is 0. The scoring results are more accurate than simply dividing the heart into regions using straight lines which approximate the regions of the heart.

By assigning each relevant plaque to a particular coronary artery, the exemplary embodiments invention support automatic scoring, where each artery can have a score that indicates its risk of cardiac diseases or heart attack. The individual scores of the arteries can provide doctors with better diagnostic information. For example, calcium in the LM artery is considered a significant disease risk and a major factor in risks for heart attacks.

The methods described herein eliminate the need for a user to manually identify the coronary arteries in the image (e.g., X-ray) and label each calcification in the image by which artery it belongs to or whether it is present in an artery at all. An exemplary, non-limiting score is as follows:

In this example, three plaques are present:

Plaque 1: inside LM, area 40 mm, maximum X-ray attenuation 150 HU.

Plaque 2: inside LCX, area 25 mm, maximum X-ray attenuation 250 HU.

Plaque 3: inside LCX, area 70 mm, maximum X-ray attenuation 140 HU.

The individual score for each of the plaques is calculated as follows in view of the weighting:

Score of Plaque 1: area 40*weight 1=40.
Score of Plaque 2: area 25*weight 2=50.
Score of Plaque 3: area 70*weight 1=70.

Based on the foregoing individual scores of the plaques, scores for coronary arteries are calculated as follows:

Score of LM=score of P1=40.
Score of LAD=0.
Score of LCX=sum of scores of P2 and P3=50+70=120.
Score of RCA=0.

Accordingly, the overall score for the heart is calculated as follows:

LM+LAD+LCX+RCA=40+0+120+0=160.

In the foregoing example, weighting may be determined by CT value (e.g., 1 for 131-200 HU, 2 for 201-300 HU, etc. in Agatston scoring). The weight does not depend on the location or the artery. In the foregoing weighting scheme, HU refers to a Hounsfield Unit, which is a unit of X-ray attenuation.

In the related art, individual scores are not calculated automatically. In contrast, in the above example, only a single score would be calculated, which is the sum of the plaques:

Score=sum of scores of all plaques=40+50+70=160.

In the related art, LM, LAD, LCX and RCA scores are not calculated.

I. Model-Based Approach Methods

Figure 2:
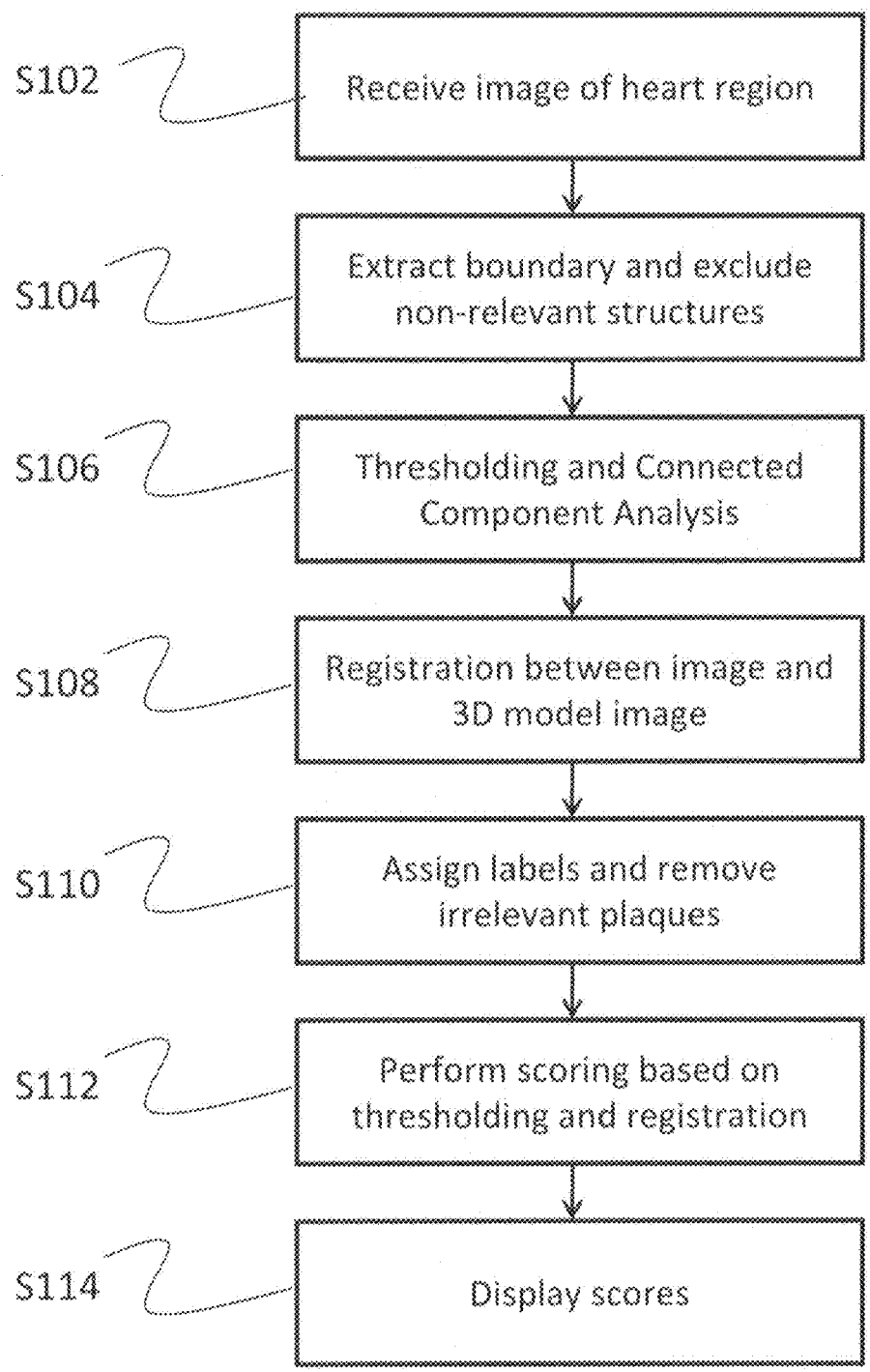
FIG. 2 depicts a method of coronary artery calcium scoring, according to one embodiment of the invention.

In one exemplary method for coronary artery calcium (CAC) scoring, illustrated in FIG. 2, an image of a heart region is received (step S102). The CT image may be a volumetric three-dimensional (3D) computed tomography (CT) image, which is a stack of a sequence of two-dimensional CT images. In step S104, the heart is extracted and the boundary is identified to exclude bones, pulmonary structures and other irrelevant anatomical features in the image. Extracting the heart may be performed as would be understood by those of ordinary skill in the art. For example, but not by way of limitation, edge-based segmentation, region growing segmentation, level-set segmentation, active contour segmentation, or model-based segmentation may be applied.

Next, in step S106, thresholding is executed inside the heart. Calcifications are easily defined in an image due to their density, as the pixels (2D) or voxels (3D) which they occupy have high values on the Hounsfield scale. Thus, calcifications are identified by simple thresholding. For example but not by way of limitation, in the Agatston scoring method, voxels with CT value larger than 130 HU are considered as potential calcium plaques.

Next, also in step S106, a connected component analysis is performed to assign a unique label to each of connected components. The connected component analysis is performed as would be understood by one of ordinary skill in the art.

A registration is then performed between the 3D CT image and a 3D model (step S108), where the 3D model is aligned with the 3D image so that the anatomical structures of the 3D model can be mapped on the 3D CT image. The 3D model must overlap the 3D CT image correctly in order to properly identify the coronary arteries in the 3D CT image. This registration will be described in further detail below. Based on the registration results, in step S110, each calcium plaque which is located in one of the identified coronary arteries can be automatically identified with much higher certainty as to whether it is located within a particular coronary artery. The calcium plaques are labeled by which coronary artery it is located in. By labeling the relevant plaques, the plaques which do not occur in the identified coronary arteries are therefore irrelevant and can be removed from consideration for the subsequent scoring process for the artery or arteries. These irrelevant plaques include aortic calcium or structures outside of the heart (e.g. bones).

In step S112, scoring is then performed based on the thresholding results and registration results. As described above, each individual artery can be individually scored, and an overall score may then be computed for the entire heart. If no calcium plaque is in an artery, the score for that artery is 0. Finally, in step S114, the scores will be displayed to a user along with any other visualizations the user prefers.

The registration and labeling steps will now be further described. There are two options for the registration process—a rough registration or simple alignment between the two images (e.g., using one user input of the left ostium location), or alternatively, a more complex convergence of identified landmarks from the two images.

In the rough registration, a basic alignment between the two images is performed to provide an approximate location for the coronary arteries in the 3D CT image. This can be performed to translate landmark points of the model to fit those in the image, with no or a small degree of rotation, scaling, or deformation. For example, if left ostium location is known by a user input or an algorithm, it can be aligned with the actual left ostium in the image, and thus, other parts of images can also be approximately aligned. Even without complicated registration, this provides reasonable accuracy in roughly dividing the heart region into regions corresponding to each of the four coronary arteries, LM, LAD, LCX and RCA and assigning coronary artery labels to calcium plaques is still possible.

Figure 3:
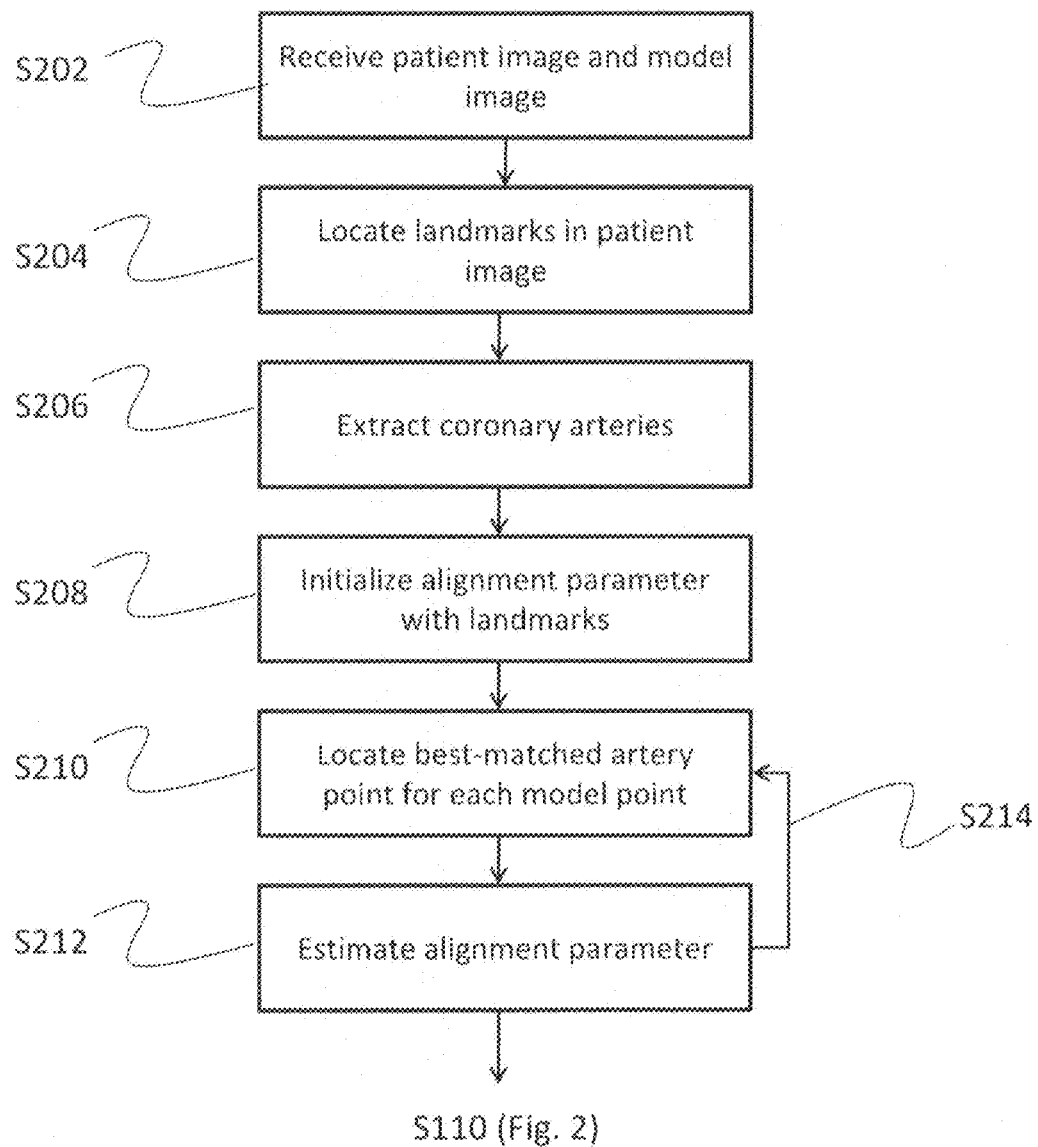
FIG. 3 depicts a method of registering an image of a heart with a model image of a heart, according to one embodiment of the invention.

In the more complex convergence-type registration, landmarks identified in the 3D volume of the heart in the CT image are aligned with landmarks identified in the 3D model image by estimating alignment parameters of matching landmarks over multiple iterations until convergence of the two images is reached. In the complex convergence-type registration, illustrated in FIG. 3, the first step S202 is to obtain the model image and the CT image. In the CT image, landmarks are identified in step S204—such as the aorta, coronary ostia, valves or apex. The landmarks can be identified manually by the user since they are typically easy to find and identify, or an image processing algorithm may automatically identify these landmarks based on their general locations and properties. For example, but not by way of limitation, an aorta may be automatically identified by an image processing algorithm based on a Hough transform.

Next, in step S206, the coronary arteries are extracted—usually by identifying fragments of the arteries since the complete image of the artery may not be easily identified. This extraction can be accomplished by identifying tubular structures in the image to be examined. For example, but not by way of limitation, an exemplary extraction process is disclosed in U.S. Patent Application Publication No. 20110135172, the contents of which is incorporated herein by reference. An alignment parameter is determined by using the landmarks identified in the previous step (step S208). The alignment parameter defines the set of angles and translations that will align the 3D model with the 3D CT image. For example, but not by way of limitation, the initial alignment is aligning the aorta of the 3D CT image with the aorta in the 3D model. Once this is complete, more detailed alignments may be performed for more specific landmarks, as would be understood by those skilled in the art. For example, in rigid registration, scaling, translation, and rotation parameters can be applied; in non-rigid registration, each grid (or mesh) point can have a displacement, where usually the displacement of a point is assumed to be substantially similar to those in its neighborhood.

Then, in step S210, for each model point, the best-matched artery point among the candidates is extracted and a correspondence is then obtained between the CT image and the model image. Using this correspondence, an alignment parameter is then estimated in step S212. The extraction of the best-matched artery points and the estimation of the alignment parameter are then repeated (step S214) until the CT image and the model image converge.

After registration, a label is assigned to each calcium plaque which identifies which of the coronary arteries the plaque is located in. The registration result with the model, or registration with a probability map may be used determine whether a particular calcium plaque is located within an identified artery. The registration process improves the ability to identify whether a particular calcium plaque occurs along the line or edge of the artery, and thus is more likely to be a vessel-based calcification that should be factored when scoring the calcifications.

Scoring can then be performed by simple arithmetic operations, which are usually weighted sum of scores of individual CAC plaques, for each artery and overall arteries.

The objective for the foregoing steps is to automatically identify, for each calcium plaque, whether or not the plaque is a false positive, such as aortic calcium or structures outside the heart, and if not, which coronary artery (LM, LAD, LCX, RCA) it belongs to.

The model image may be a point-model, such as that derived from Dodge Jr., J. T., et al.: Intrathoracic Spatial Location of Specified Coronary Segments on the Normal Human Heart. Circulation 78, 1167-1180 (1988). An alternative which may provide an improved model would be using existing CAT segmentations/labeling to augment the model. With a great deal of segmented/classified data already obtained, the existing CAT segmentations/labeling data could be added to the model. The model can be a point-model, a shape model, a probability model, or any such model as would be understood by one skilled in the art. More data should reduce the variance and increase the accuracy of the model image.

In extracting the fragments of coronary arteries (S206), the segmentation may not need to be as perfect as with coronary artery extraction in contrasted CT data. The registration does not have to be highly accurate, as it only needs to be sufficient to identify roughly which part of the heart in the patient image would correspond to a region where a certain coronary artery is usually located. In this sense, exact segmentation of a coronary artery would not be needed, as a rough or discontinued segmentation—or even no segmentation—would suffice. For example, even in a worst case where few reasonable candidate vessels are available by segmentation, instead of the registration consisting of initializing the alignment parameter (S208), locating the best-matched artery points (S210), estimating the alignment parameter (S212) and repeating until convergence is achieved (S214), a method could be performed to 1) first align the model with the heart and 2) then simply assign the nearest artery in the model to each plaque.

In many cases, there are plaques that are not coronary artery calcium but other structures, such as aortic calcium, bones, pulmonary structures, noise, etc., and by assigning labels to the connected components (S110), the non-labeled, irrelevant plaques can be removed from consideration when scoring is performed. Although step S108 provides information about which plaque is within a region of which artery, there are more factors to consider when determining whether or not the plaque is really coronary artery calcium. Even when a plaque is determined to be within a realm of a certain coronary artery, the determination could be a false positive. For this reason, in step S110 various factors of the plaques are considered, such as direction, vesselness, relation to other plaques, shapes, etc., before making a decision as to whether the plaque should be labeled to a particular coronary artery or whether it is irrelevant. In the decision making process, pattern classification methods, such as support vector machine (SVM), neural networks, linear classifier, etc., could be used.

Figure 4:
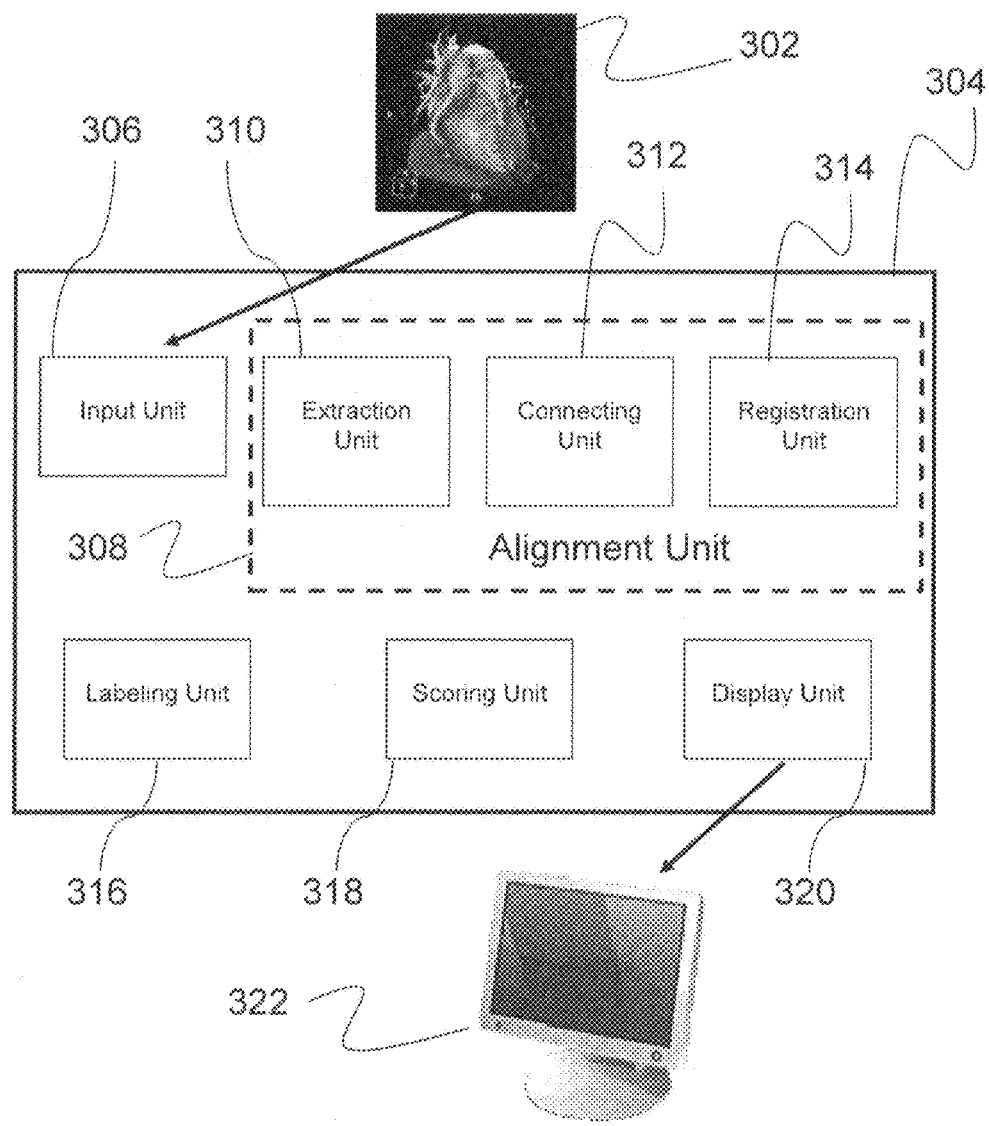
FIG. 4 depicts a system for coronary artery calcium scoring, in accordance with one embodiment of the invention.

The inventive system may be implemented on a computer which receives the medical image and processes it according to the steps described above. The inventive system may be embodied as a computer program product or carried out by a combination of software and hardware. As illustrated in FIG. 4, an image 302 may be input to a computer 304 at an input unit 306. A alignment unit 308 then matches anatomical features of the heart in the image with anatomical features of a model image. The alignment unit 308 may include an extraction unit 310, connecting unit 312 and registration unit 314. The extraction unit 310 extracts the heart boundary (S206) to exclude bones, pulmonary structures and other irrelevant plaques. At the connecting unit 312, thresholding is executed inside the heart and a connected component analysis is performed. A registration is then performed between the CT image and a 3D model via the registration unit 314. At the labeling unit 316, irrelevant plaques, such as aortic calcium or structures outside of the heart (e.g. bones) can be removed from consideration for the subsequent scoring. The registration results also allow a coronary artery label to be assigned for each connected component. Scoring is then performed at the scoring unit 318 based on the thresholding results and registration results. Finally, a display unit 320 prepares a graphical user interface (GUI) for displaying the scores to a user along with any other visualizations the user prefers on a screen 322.

The inventive systems and methods are applicable to many types of medical imaging, including but not limited to magnetic resonance imaging (MRI), radiography (x-rays), computed tomography (CT) and ultrasound (US).

II. Dynamic Updating of Calcium Scores

In another embodiment, the model-based approach could be used for dynamic updating of calcium scoring. Initially, the full scoring may not be obtained right away, and if it is not, as soon as the user selects and classifies a single plaque of calcium on the image, the selection will dramatically change the understanding of where certain vessels are located. Thus, the system can dynamically rescore the arteries as the plaques are selected. For example, as soon as a plaque is marked LAD, all "downstream" plaques that seem to follow a reasonable path of a vessel are more likely to be LAD plaques. In this process, the comparison of the model and the plaques may play crucial roles.

III. Computer Embodiment

Figure 5:
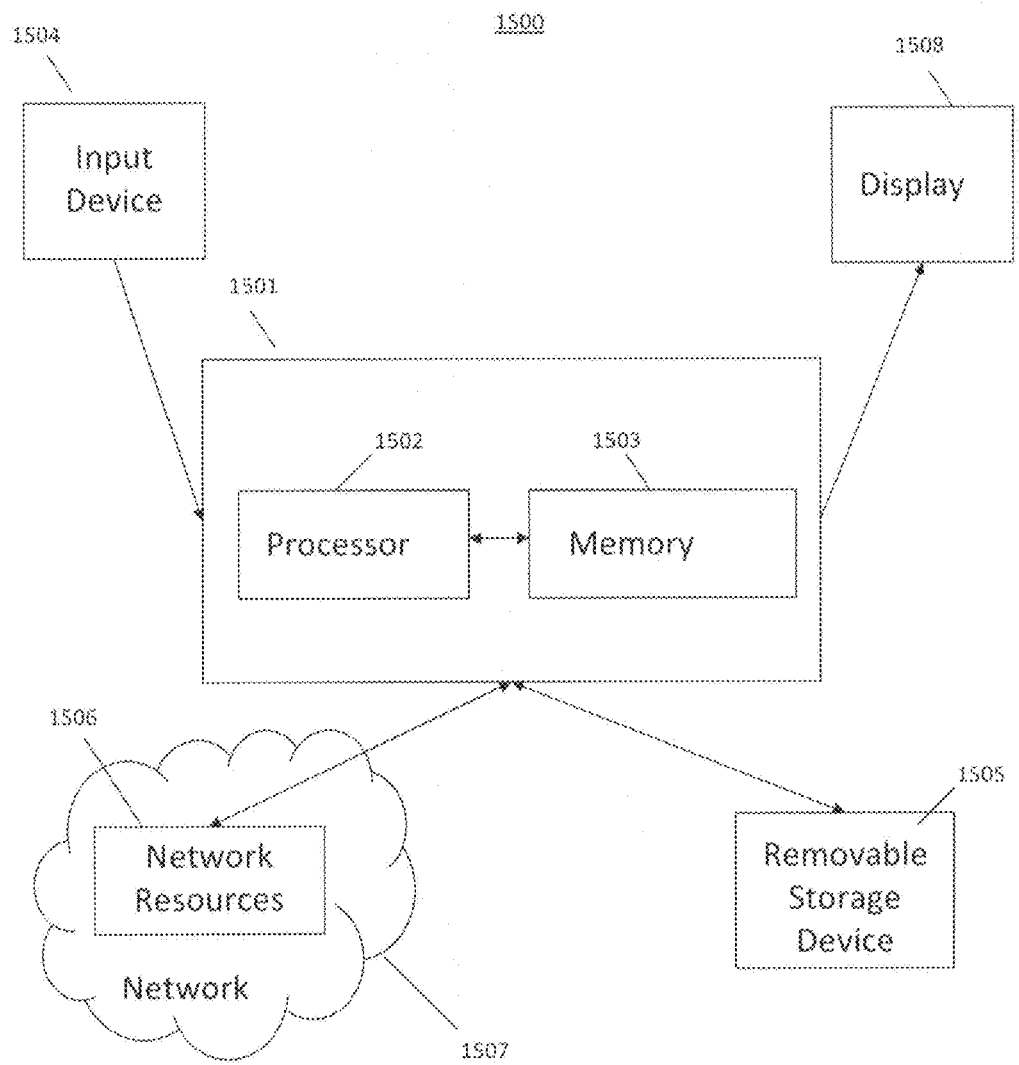
FIG. 5 illustrates an exemplary embodiment of a computer platform upon which the inventive system may be implemented.

FIG. 5 is a block diagram that illustrates an embodiment of a computer/server system 1500 upon which an embodiment of the inventive methodology may be implemented. The system 1500 includes a computer/server platform 1501 including a processor 1502 and memory 1503 which operate to execute instructions, as known to one of skill in the art. The term "computer-readable storage medium" as used herein refers to any tangible medium, such as a disk or semiconductor memory, that participates in providing instructions to processor 1502 for execution. Additionally, the computer platform 1501 receives input from a plurality of input devices 1504, such as a keyboard, mouse, touch device or verbal command. The computer platform 1501 may additionally be connected to a removable storage device 1505, such as a portable hard drive, optical media (CD or DVD), disk media or any other tangible medium from which a computer can read executable code. The computer platform may further be connected to network resources 1506 which connect to the Internet or other components of a local public or private network. The network resources 1506 may provide instructions and data to the computer platform from a remote location on a network 1507. The connections to the network resources 1506 may be via wireless protocols, such as the 802.11 standards, Bluetooth® or cellular protocols, or via physical transmission media, such as cables or fiber optics. The network resources may include storage devices for storing data and executable instructions at a location separate from the computer platform 1501. The computer interacts with a display 1508 to output data and other information to a user, as well as to request additional instructions and input from the user. The display 1508 may therefore further act as an input device 1504 for interacting with a user.

Although various representative embodiments of this invention have been described above with a certain degree of particularity, those skilled in the art could make numerous alterations to the disclosed embodiments without departing from the spirit or scope of the inventive subject matter set forth in the specification and claims. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. Also, various aspects and/or components of the described embodiments may be used singly or in any combination in the computerized storage system. It is intended that all matter contained in the above description or shown in the accompanying drawings shall be interpreted as illustrative only and not limiting.

What is claimed is:

1. A method for coronary artery calcium scoring, the method using one or more processors, comprising:
receiving an image of a heart;
registering anatomical features of the heart in the image with anatomical features of a model image illustrating coronary arteries of a heart;
using one or more processors, to identify a plurality of coronary arteries in the image of the heart with reference to the coronary arteries in the model image based on a result of the registering between the image of the heart and the model image,
using one or more processors to determine, for each respective plurality of plaques appearing in the image of the heart, that a respective plaque is determined to be in one of the identified plurality of coronary arteries or that the respective plaque is not present in any of the identified plurality of coronary arteries;
using one or more processors, to label each respective one of the plurality of plaques which is determined to be present in the identified coronary arteries in the image of the heart to a respective coronary artery in which the plaque is present based on a result of the determining;
scoring each respective artery of the identified plurality of coronary arteries to determine individual coronary artery calcium scores for the respective coronary arteries based on a result of the labeling and a result of the determining as to which of the identified plurality of coronary arteries a plaque is present or the plaque is not present in the identified plurality of coronary arteries, modifying the individual coronary artery calcium scores of the respective coronary arteries using weight factors based on X-ray attenuation for the respective plaques and determining an overall coronary artery calcium score for the heart by adding the modified individual coronary artery calcium scores; and
displaying the individual coronary artery calcium scores and the overall coronary artery calcium score.

2. The method of claim 1, wherein the image of the heart and the model image are three-dimensional (3D) volumetric images.

3. The method of claim 1, further comprising aligning anatomical features by identifying landmarks on the image.

4. The method of claim 3, further comprising aligning landmarks on the image with landmarks on the model image to identify the anatomical features in the image.

5. The method of claim 4, further comprising determining an alignment parameter between the matched landmarks.

6. The method of claim 5, further comprising locating anatomical features on the image which best match anatomical features on the model image.

7. The method of claim 6, further comprising estimating an alignment parameter between the matched anatomical features.

8. The method of claim 1, wherein in scoring each of the coronary arteries, a plaque which is determined not to be present in the any of the plurality of identified coronary arteries is removed from consideration.

9. The method of claim 1, wherein the registering step includes matching the image of the heart and the model image to distinguish automatically whether plaque is occurring in the plurality of identified coronary arteries in comparison to plaque occurring in irrelevant anatomical features which do not correspond to coronary arteries.

10. The method of claim 1, wherein the determination for each respective plurality of plaques appearing in the image of the heart, that a respective plaque is determined to be in one of the identified plurality of coronary arteries, or that the respective plaque is determined to be not present in any of the identified plurality of coronary arteries is determined automatically.

11. A system for coronary artery calcium scoring, the system comprising:
an input unit which receives an image of a heart;
a register unit which matches anatomical features of the heart in the image with anatomical features of a model image illustrating coronary arteries of a heart;
an identifying processing unit configured to identify a plurality of coronary arteries in the image of the heart with reference to the coronary arteries in the model image based on a match result of the register unit between the image of the heart and the model image;
a determining processing unit, configured to determine for each respective plurality of plaques appearing in the image of the heart, that a respective plaque is determined to be one of the identified plurality of arteries or that the respective plaque is not present in any of the identified plurality of coronary arteries;
a labeling processing unit which is configured to label each respective one of the plurality of plaques which is determined to be present in the identified coronary arteries in the image of the heart to a respective coronary artery in which the plaque is present based on a result of the determining processing unit;
a scoring unit which scores each respective artery of the identified plurality of the coronary arteries to determine individual coronary artery calcium scores for the respective coronary arteries based on a result of the labeling processing unit and a result of the determining processing unit as to which of the identified plurality of coronary arteries a plaque is present or the plaque is not present in the identified plurality of coronary arteries, modifies the individual coronary artery calcium scores of the respective coronary arteries using weight factors based on X-ray attenuation for the respective plaques and determines an overall coronary artery calcium score for the heart by adding the modified individual coronary artery calcium scores; and
a display unit which prepares a graphical user interface for displaying the individual coronary artery calcium scores and the overall coronary artery calcium score.

12. The system of claim 11, wherein the image of the heart and the model image are three-dimensional (3D) volumetric images.

13. The system of claim 11, wherein the alignment unit further comprises an extraction unit which identifies a boundary of the heart.

14. The system of claim 13, wherein the alignment unit further comprises a connecting unit which performs a connected component analysis.

15. The system of claim 14, wherein the alignment unit further comprises a registration unit which aligns the image with the model image using an alignment parameter.

16. A non-transitory computer program product for coronary artery calcium scoring, the computer program product embodied on a computer readable medium and when executed by a computer, performs the method comprising:

receiving an image of a heart;

registering anatomical features of the heart in the image with anatomical features of a model image illustrating coronary arteries of a heart;

using a result of the registering between the image of the heart and the model image to identify a plurality of coronary arteries in the image of the heart based on a result of the registering;

determining for each respective plurality of plaques appearing in the image of the heart, that a respective plaque is determined to be in one of the identified plurality of coronary arteries or that the respective plaque is not present in any of the identified plurality of coronary arteries;

labeling each respective one of the plurality of plaques which is determined to be located within the one of the plurality of the identified coronary arteries on the image of the heart to a respective coronary artery in which the plaque is present based on a result of the determining;

scoring each respective artery of the identified plurality of coronary arteries to determine individual coronary artery calcium scores for the respective coronary arteries based on a result of the labeling and a result of the determining as to which of the identified plurality of coronary arteries a plaque is present or the plaque is not present in the identified plurality of coronary arteries, modifying the individual coronary artery calcium scores of the respective coronary arteries using weight factors based on X-ray attenuation for the respective plaques and determining an overall coronary artery calcium score for the heart; and displaying the individual coronary artery calcium scores and the overall coronary artery calcium score.

* * * * *